US012605048B2

(12) United States Patent
Nakanishi et al.

(10) Patent No.: US 12,605,048 B2
(45) Date of Patent: Apr. 21, 2026

(54) STERILIZED MEDICAL DEVICE WITH TEARABLE COVER

(71) Applicant: OLYMPUS MEDICAL SYSTEMS CORP., Tokyo (JP)

(72) Inventors: Nobuyuki Nakanishi, Hino (JP); Keita Ozawa, Hino (JP); Hiroaki Osawa, Saitama (JP); Masahiro Ashizuka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 518 days.

(21) Appl. No.: 18/102,880

(22) Filed: Jan. 30, 2023

(65) Prior Publication Data

US 2023/0248221 A1 Aug. 10, 2023

Related U.S. Application Data

(60) Provisional application No. 63/307,694, filed on Feb. 8, 2022.

(51) Int. Cl.
*A61B 1/00* (2006.01)

(52) U.S. Cl.
CPC ................................. *A61B 1/00144* (2013.01)

(58) Field of Classification Search
CPC ............................ A61B 1/00144; A61B 1/018
See application file for complete search history.

(56) References Cited

U.S. PATENT DOCUMENTS

| 4,779,611 A | * | 10/1988 | Grooters | ............ | A61B 1/00082 |
| | | | | | 600/116 |
| 2018/0228348 A1 | * | 8/2018 | Yamaya | .................. | G02B 23/16 |
| 2019/0167078 A1 | * | 6/2019 | Fryer | ................. | A61B 1/00142 |
| 2019/0208992 A1 | | 7/2019 | Yamaya | | |

FOREIGN PATENT DOCUMENTS

| JP | H08-173376 A | 7/1996 |
| JP | 2008-167772 A | 7/2008 |
| JP | 2017-058156 A | 3/2017 |
| JP | 2019-099277 A | 6/2019 |

* cited by examiner

*Primary Examiner* — Erin Mcgrath
(74) *Attorney, Agent, or Firm* — Morgan, Lewis & Bockius LLP

(57) ABSTRACT

A medical device includes: a first sterilized insertion device including an insertion portion configured to be inserted into a subject, and a cover surrounding a distal end portion of the insertion portion. The cover is configured to be teared by receiving external force so as to make an opening in the cover for exposing the distal end portion.

16 Claims, 9 Drawing Sheets

STERILIZED MEDICAL DEVICE WITH TEARABLE COVER

RELATED APPLICATION DATA

This application is based on and claims priority under 35 U.S.C. § 119 to U.S. Provisional Application No. 63/307, 694 filed on Feb. 8, 2022, the entire contents of which are incorporated herein by reference.

FIELD OF THE DISCLOSURE

The present disclosure relates to a medical device to which sterilizing treatment is applied.

BACKGROUND

In recent years, for medical devices, such as endoscopes or treatment instruments, used in a medical field, single-use medical devices that are discarded after being used one time have been used. Sterilizing treatment is applied to such medical devices before shipping, and the medical devices are sealed in a packaging material, such as a sterilization pack, while maintaining a sterilized state.

A treatment instrument taken out of the packaging material is inserted through a treatment instrument insertion channel of an endoscope and, thereafter, is caused to protrude from a distal end portion of an insertion portion of the endoscope to be used for various treatments applied to lesions or the like.

Japanese Patent Application Laid-Open Publication No. H8-173376, for example, discloses a side-viewing endoscope. In such a side-viewing endoscope, a treatment instrument inserted through a treatment instrument insertion channel has a direction of protrusion changed by a treatment instrument raising base (forceps elevator) provided to a distal end portion of an insertion portion of the endoscope, and is caused to protrude from an opening provided in a side surface of the distal end portion of the insertion portion of the endoscope.

SUMMARY OF THE DISCLOSURE

A medical device includes: a first sterilized insertion device including an insertion portion configured to be inserted into a subject, and a cover surrounding a distal end portion of the insertion portion. The cover is configured to be teared by receiving external force so as to make an opening in the cover for exposing the distal end portion.

DETAILED DESCRIPTION

In general, a single-use medical device is sealed in a packaging material, such as a sterilization pack, after sterilizing treatment is applied to the single-use medical device and hence, there is a low risk of bacteria, such as environmental bacteria, adhering to the single-use medical device.

According to embodiments described hereinafter, it is possible to provide a medical device that can reduce a possibility of bacteria adhering to a single-use medical device after the medical device is taken out of a packaging material. Hereinafter, embodiments will be described in detail with reference to drawings.

Note that the drawings based on the embodiments are schematic views, and a relationship between thicknesses and widths of respective portions, a ratio between thicknesses and relative angles of the respective portions, for example, may differ from actual ones. The dimensional relations and the ratio may differ in some parts between the drawings.

First Embodiment

Figure 1:
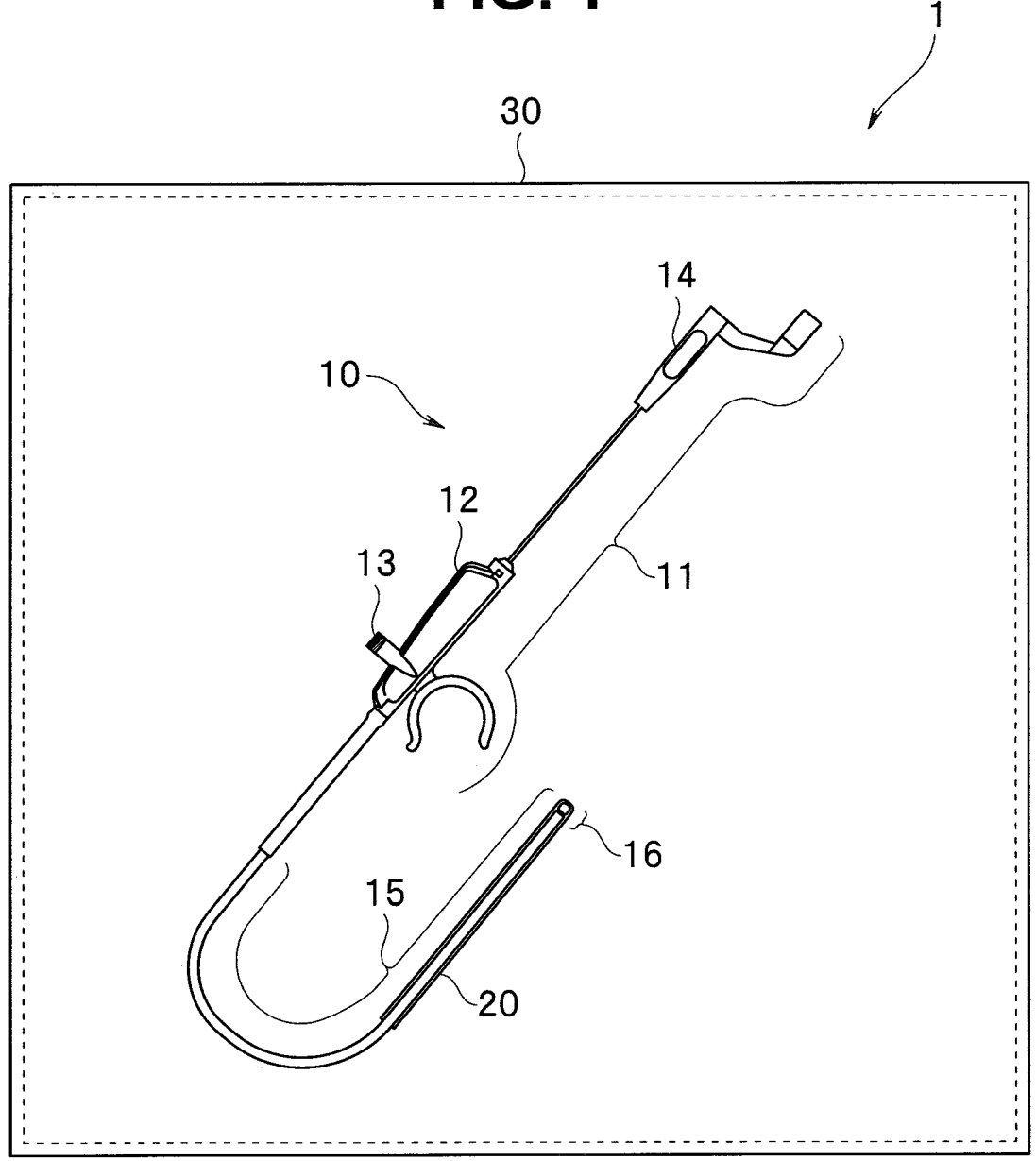
FIG. 1 is a diagram showing one example of an overall configuration of a medical device according to a first embodiment.
Figure 2:
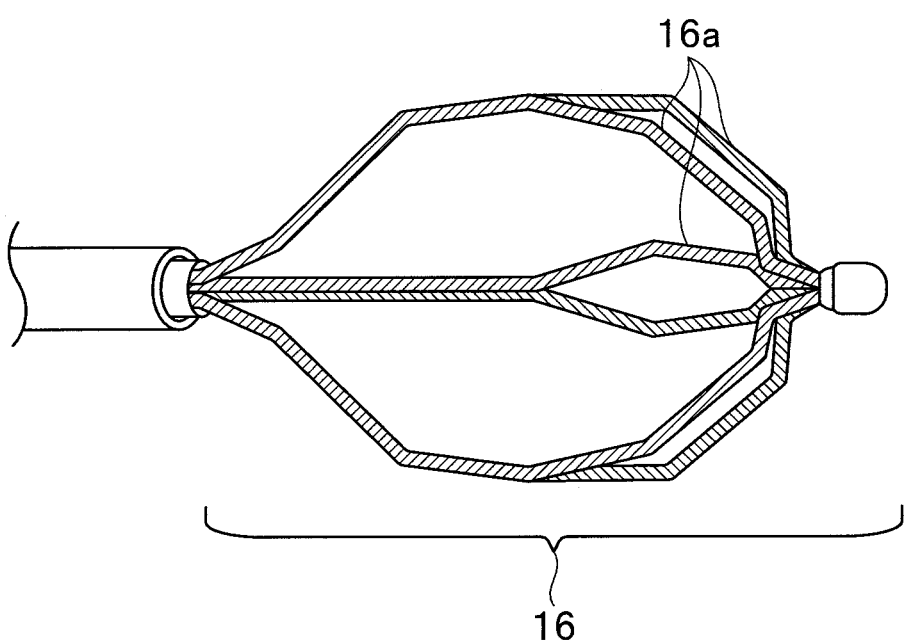
FIG. 2 is a diagram showing one example of a grasping portion of a treatment instrument in an open state.

FIG. 1 is a diagram showing one example of an overall configuration of a medical device according to a first embodiment, and FIG. 2 is a diagram showing one example of a grasping portion of a treatment instrument 10 in an open state. A medical device 1 shown in FIG. 1 includes a treatment instrument 10, a cover 20, and a sterilization packaging material 30.

The treatment instrument 10 is a long insertion device that is to be inserted into a body. The treatment instrument 10 is, for example, a disposable stone-catching basket that grasps and recovers calculi. Note that the treatment instrument 10 is not limited to the disposable stone-catching basket, and may be another treatment instrument.

The treatment instrument 10 includes an operation portion 11 and an insertion portion 15 configured to be inserted into a subject. The operation portion 11 includes an operation portion body 12, a liquid feeding pipe sleeve 13, and a tab 14, the liquid feeding pipe sleeve 13 being provided to the operation portion body 12. A syringe, for example, is connected to the liquid feeding pipe sleeve 13, thus allowing feeding of a medicinal solution, such as a contrast agent.

The insertion portion 15 includes a grasping portion 16 at a distal end portion. When an operator pushes the tab 14 into the operation portion body 12, as shown in FIG. 2, the grasping portion 16 protrudes from a distal end of the insertion portion 15. The grasping portion 16 includes a plurality of basket wires 16a. When the tab 14 is pushed into the operation portion body 12, the plurality of basket wires 16a are caused to protrude from the distal end portion of the insertion portion 15 in an open state.

The operator takes a calculus, for example, into the plurality of basket wires 16a in an open state, and then pulls the tab 14 relative to the operation portion body 12. With such operations, the plurality of basket wires 16a are housed in the distal end portion of the insertion portion 15, thus being closed and hence, the grasping portion 16 can grasp the calculus.

The cover 20 is provided to cover the insertion portion 15 of the treatment instrument 10. A proximal end portion of the cover 20 is bonded to the insertion portion 15. Such a configuration maintains watertightness of the distal end portion of the insertion portion 15 of the treatment instrument 10. When the cover 20 receives a predetermined external force, an opening is formed, the grasping portion 16 of the treatment instrument 10 being exposed from the opening. The cover 20 surrounds the distal end portion of the insertion portion 15. The cover is configured to be teared by receiving external force so as to make an opening in the cover 20 for exposing the distal end portion of the insertion portion 15. The distal end portion of the insertion portion 15 has an outer surface and an end surface. The cover 20 may completely surround the outer surface and the end surface. The cover 20 completely surrounds the outer surface and the end surface so as to encase the outer surface and the end surface within the cover 20 to maintain the encased portions sterilized. The insertion portion 15 includes the distal end portion and a proximal end portion, and the proximal end portion is not surrounded by the cover 20. The opening in the cover may be at a distal end of the cover 20.

The sterilization packaging material 30 is sealed in a state in which the treatment instrument 10 and the cover 20 are disposed in the sterilization packaging material 30. Thereafter, the sterilization packaging material, in which the treatment instrument 10 and the cover 20 are disposed, is placed in a sterilization device, and sterilizing treatment is then applied. With such sterilizing treatment, the treatment instrument 10, the cover 20, and the sterilization packaging material are sterilized. The treatment instrument 10 taken out of the sterilization packaging material 30 is inserted through a treatment instrument channel of the endoscope with the insertion portion 15 covered by the cover 20, and is caused to protrude from a distal end forming portion of the endoscope.

Figure 3:
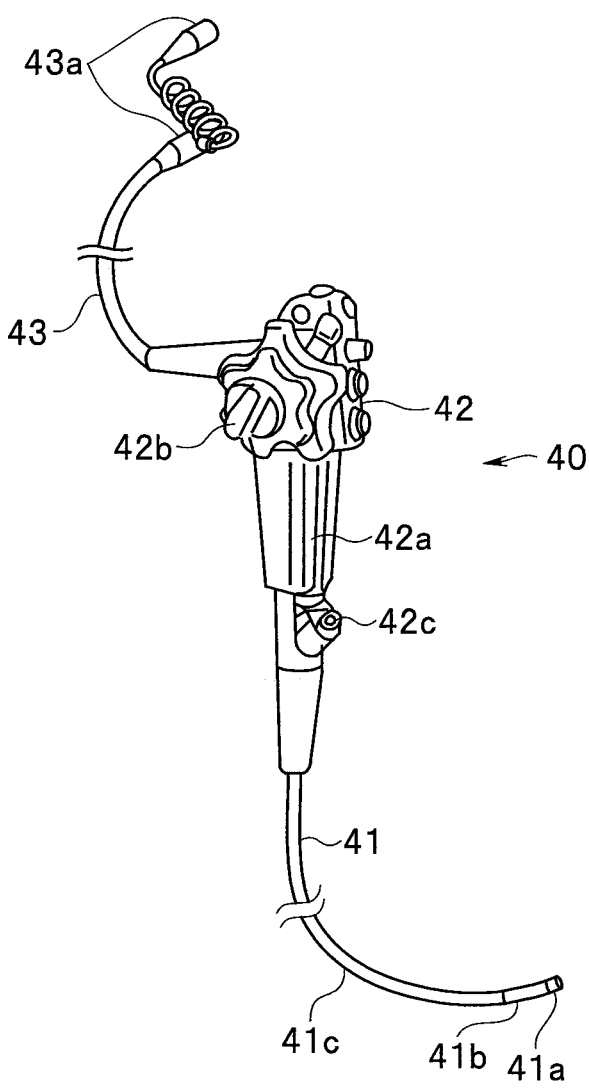
FIG. 3 is a diagram showing a configuration of an endoscope having a treatment instrument channel through which the treatment instrument is inserted.
Figure 4:
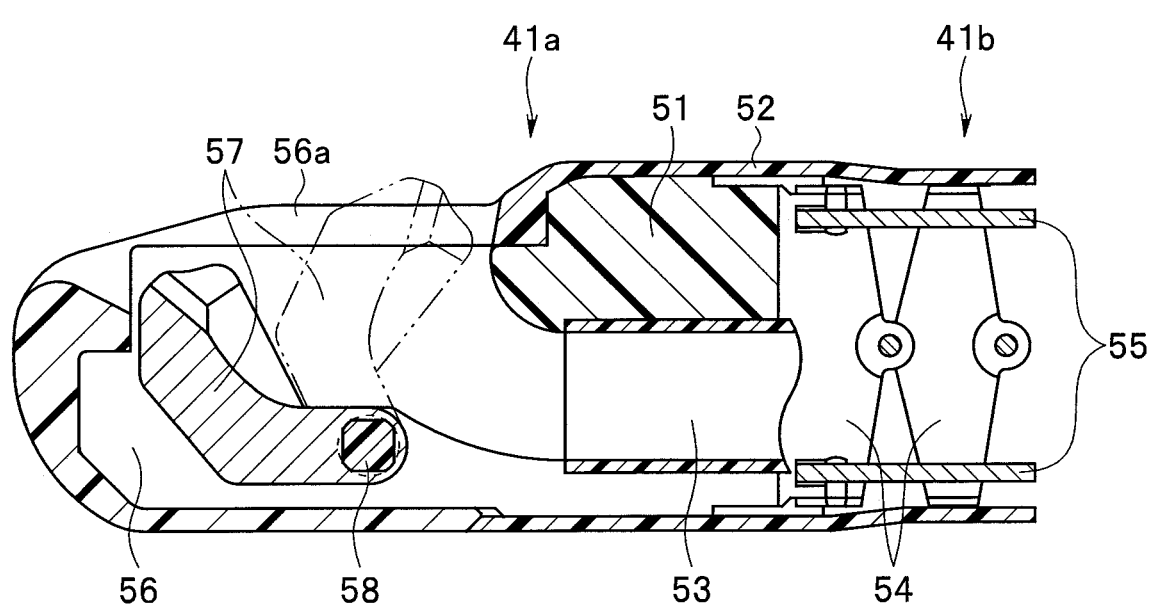
FIG. 4 is a cross-sectional view showing a constitutional example in which a treatment instrument raising base is provided to a distal end forming portion of the endoscope, the treatment instrument raising base changing a direction of the treatment instrument that protrudes from the treatment instrument channel.

FIG. 3 is a diagram showing a configuration of the endoscope having the treatment instrument channel through which the treatment instrument is inserted. FIG. 4 is a cross-sectional view showing a constitutional example in which a treatment instrument raising base is provided to the distal end forming portion of the endoscope, the treatment instrument raising base changing a direction of the treatment instrument that protrudes from the treatment instrument channel.

As shown in FIG. 3, an endoscope 40 includes an insertion portion 41, an operation portion 42, and a universal cable 43.

The insertion portion 41 is an elongated portion that is to be inserted into a body cavity of a subject. It is anticipated that one example of the subject into which the insertion portion 41 is inserted is a human body. However, the subject is not limited to the human body, and may be a living object, such as an animal, or may be a non-living object, such as a machine or a building.

The insertion portion 41 includes, from a distal end side toward a proximal end side, a distal end forming portion 41a, an active bending portion 41b, and a flexible tube portion 41c in this order.

As shown in FIG. 4, a distal end portion body 51 is provided to the distal end forming portion 41a, and a cylindrical exterior member 52 is provided on an outside of internal components, including the distal end portion body 51, in the insertion portion 41. Inner portions of the exterior member 52 and the distal end portion body 51 form a lumen. Various internal components, such as an image pickup unit (not shown in the drawing) and a light guide (not shown in the drawing), are accommodated in the lumen in addition to a treatment instrument channel 53, bending pieces 54, and bending wires 55, the image pickup unit picking up an image of an object, the light guide illuminating the object.

A housing chamber 56 that communicates with the treatment instrument channel 53 is provided in the distal end portion body 51. The housing chamber 56 has an opening 56a forming an opening portion on one side surface of the distal end forming portion 41a.

A treatment instrument raising base 57 is disposed in the housing chamber 56, and is turnably supported by a support shaft 58. A raising wire not shown in the drawing is connected to the treatment instrument raising base 57. When the raising wire is pulled, the treatment instrument raising base 57 turns from a standby position indicated by a solid line to a raised position indicated by a dashed-and-double-dotted line.

When the treatment instrument raising base 57 turns to the raised position in a state in which the treatment instrument 10 protruding from the treatment instrument channel 53 is disposed on the treatment instrument raising base 57, a distal end portion of the treatment instrument 10 is raised, thus protruding from the opening 56a.

The active bending portion 41b is a bendable portion disposed on a proximal end side of the distal end forming portion 41a. The active bending portion 41b is configured to be bendable in two directions or in four directions of an upward direction, a downward direction, a leftward direction, and a rightward direction, for example.

In the active bending portion 41b, as shown in FIG. 4, a plurality of bending pieces 54 are continuously provided in a swingable manner in a longitudinal axis of the insertion portion 41, and the bending wires 55 are connected to a bending piece 54 disposed at a distal end. Proximal ends of the bending wires 55 are connected to a bending operation knob 42b of the operation portion 42.

When the active bending portion 41b is bent, a direction of the distal end forming portion 41a changes, thus changing an observation direction of the image pickup unit and a direction in which irradiation is performed with illumination light from the light guide. The active bending portion 41b is also bent to increase ease of insertion of the insertion portion 41 in the subject.

The flexible tube portion 41*c* is a tube portion disposed on a proximal end side of the active bending portion 41*b* and having flexibility.

The operation portion 42 is disposed on a proximal end side of the insertion portion 41, and includes a grasping portion 42*a*, the bending operation knob 42*b*, and a treatment instrument insertion opening 42*c*. The grasping portion 42*a* is a portion where the operator grasps the endoscope 40 with a palm of a hand. The bending operation knob 42*b* is an operation device used for performing an operation of bending the active bending portion 41*b* with a thumb, for example, of the hand grasping the grasping portion 42*a*. When the bending operation knob 42*b* is operated, the bending wires 55 are pulled, so that the active bending portion 41*b* is bent. Various buttons for operating the endoscope 40 are also provided to the operation portion 42. The treatment instrument insertion opening 42*c* is an opening that communicates with the treatment instrument channel 53, and that allows insertion of the treatment instrument 10 into the treatment instrument channel 53.

The universal cable 43 extends from a side surface of the operation portion 42 on a proximal end side, for example, and is provided with a connector 43*a* at an extension end to connect the universal cable 43 to a light source device and an endoscope control device.

Figure 5A:
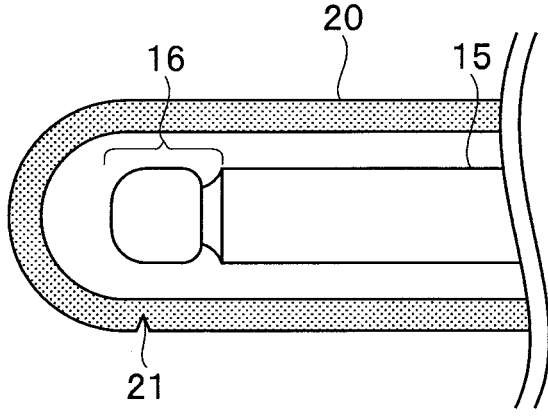
FIG. 5A is a diagram showing a configuration of the grasping portion of the treatment instrument in a state in which the grasping portion is covered by a cover.
Figure 5B:
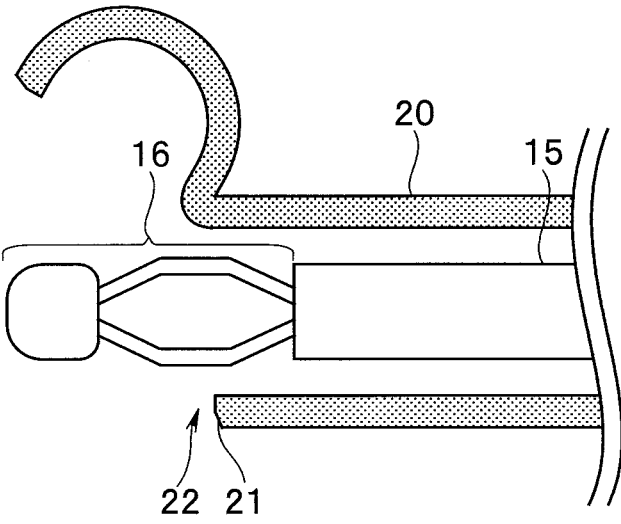
FIG. 5B is a diagram showing a configuration of the grasping portion of the treatment instrument in a state in which the grasping portion protrudes from the cover.

FIG. 5A is a diagram showing a configuration of the grasping portion of the treatment instrument in a state in which the grasping portion is covered by a cover, and FIG. 5B is a diagram showing a configuration of the grasping portion of the treatment instrument in a state in which the grasping portion protrudes from the cover.

The cover 20 is formed by connecting outermost edge portions of two films, each having a semicircular distal end, by thermocompression bonding, for example. A distal end portion of the cover 20 is provided with an easy-to-open portion 21 to which easy-to-open processing is applied to allow the easy-to-open portion 21 to be opened more easily than other portions.

The easy-to-open portion 21 (first area) is a notched portion provided to one of the outermost edge portions of the cover 20 in a longitudinal direction. As shown in FIG. 5B, the easy-to-open portion 21 is provided only to one of the outermost edge portions of the cover 20 in the longitudinal direction to prevent the distal end portion of the cover 20 from falling in the body and being left when the grasping portion 16 protrudes from the cover 20. The cover 20 includes a first area 21, and a second area adjacent the first area 21. The first area 21 is configured to be teared more easily than the second area, and the opening is formed in the first area 21. The opening may be formed at an interface of the first area 21 and the second area. The opening may be formed in the first area 21 and extends around an entire circumference of the cover 20. The distal end of the insertion portion 15 is translatable, and the first area 21 of the cover 20 is located in a direction of protrusion of the insertion portion 15.

The operator opens the sterilization packaging material 30 to take out the treatment instrument 10 with the insertion portion 15 covered by the cover 20, and then inserts the insertion portion 15 of the treatment instrument 10 into the treatment instrument insertion opening 42*c* of the endoscope 40 with the insertion portion 15 of the treatment instrument 10 covered by the cover 20. The operator inserts the insertion portion 15 of the treatment instrument 10 into the treatment instrument insertion opening 42*c* such that the grasping portion 16 provided at the distal end of the insertion portion 15 protrudes from the treatment instrument channel 53 and is disposed on the treatment instrument raising base 57. Then, when the operator turns the treatment instrument raising base 57 to the raised position, the grasping portion 16 protrudes from the opening 56*a* provided in one side surface of the distal end forming portion 41*a*.

After the grasping portion 16 of the treatment instrument 10 arrives at a position that can reach a part to be treated, when the operator pushes the tab 14 into the operation portion body 12, the grasping portion 16 protrudes from the distal end portion of the treatment instrument 10, thus applying a predetermined external force to the cover 20. With such an operation, as shown in FIG. 5B, the easy-to-open portion 21 is torn, so that an opening 22 is formed in the cover 20 and the grasping portion 16 of the treatment instrument 10 is exposed from the cover 20. The operator can apply treatment, for example, can grasp a calculus. The opening 22 is a slit formed at a position closer to a proximal end side than the distal end of the cover 20. The slit is formed to extend in a direction intersecting with the longitudinal direction of the cover 20. The first area 21 includes the slit extending in a circumferential direction of the cover 20 or in a thickness direction of the cover 20. A portion of the cover 20 that is teared to form the opening includes a distal end cover portion and a proximal end cover portion, and the proximal end cover portion is connected to the distal end cover with the opening.

As described above, after the treatment instrument 10 is taken out of the sterilization packaging material 30, there is no possibility of the grasping portion 16 of the treatment instrument 10 coming into contact with air in an operating room, body fluid of a patient or the like until the grasping portion 16 protrudes from the opening 22 formed in the easy-to-open portion 21. Accordingly, it is possible to reduce a risk of bacteria adhering to the grasping portion 16 of the treatment instrument 10 to an extremely low level. The first area 21 of the cover 20 has a first cross-sectional area, and the second area of the cover 20 has a second cross-sectional area. The first cross-sectional area 21 is smaller than the second cross-sectional area. The first area 21 of the cover 20 has a first mechanical strength, and the second area of the cover 20 has a second mechanical strength. The first mechanical strength is smaller than the second mechanical strength. The treatment instrument 10 is configured to move relative to the cover 20 in the longitudinal direction of the cover 20.

Therefore, the medical device 1 can reduce a risk of bacteria adhering to a single-use medical device after the medical device is taken out of the packaging material.

(Modification 1)

Next, a modification 1 of the first embodiment will be described.

Figure 6:
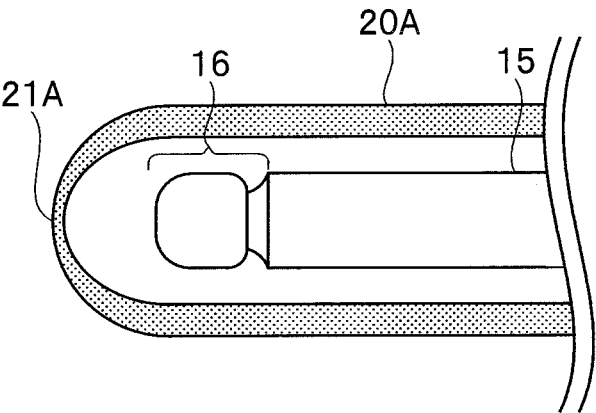
FIG. 6 is a diagram showing a configuration of a grasping portion of a treatment instrument according to a modification 1 of the first embodiment in a state in which the grasping portion is covered by a cover.

FIG. 6 is a diagram showing a configuration of a grasping portion of a treatment instrument according to the modification 1 of the first embodiment in a state in which the grasping portion is covered by a cover.

A cover 20A is formed by a member having a hemispherical distal end portion and a cylindrical proximal end portion disposed at a position closer to a proximal end side than the distal end portion. The cover 20A includes an easy-to-open portion 21A at a distal end portion. More specifically, the easy-to-open portion 21A is formed at a distal end of the distal end portion of the cover 20A, the grasping portion 16 abutting against the distal end of the distal end portion when the grasping portion 16 protrudes. The easy-to-open portion 21A formed at the distal end portion of the cover 20A is configured to have a smaller wall thickness than other portions, thus being easily torn. The easy-to-open portion 21A is configured to have a lower strength than other portions of the cover 20A. The first area 21A of the cover 20A has a first cross-sectional area, and the second area of the cover 20A has a second cross-sectional area. The first cross-sectional area 21A is smaller than the second cross-sectional area. The first area 21A of the cover 20A has a first mechanical strength, and the second area of the cover 20A has a second mechanical strength. The first mechanical strength is smaller than the second mechanical strength.

In other words, when an operator causes the treatment instrument 10 to protrude from the opening 56a, provided in one side surface of the distal end forming portion 41a and, thereafter, pushes the tab 14 into the operation portion body 12, the grasping portion 16 protrudes, thus applying a predetermined external force to the easy-to-open portion 21A of the cover 20A. With such operations, the grasping portion 16 pushes against and breaks the easy-to-open portion 21A having a smaller wall thickness than other portions, so that an opening is formed in the easy-to-open portion 21A. The opening is a slit formed to extend in a radial direction of the cover 20A, and the grasping portion 16 protrudes from the formed slit.

The cover 20A prevents the grasping portion 16 of the treatment instrument 10 from coming into contact with air in an operating room, body fluid of a patient or the like until the grasping portion 16 of the treatment instrument 10 pushes against and breaks the easy-to-open portion 21A formed at the distal end portion of the cover 20A. As a result, it is possible to reduce a risk of bacteria adhering to the grasping portion 16 of the treatment instrument 10 to an extremely low level.

Therefore, in the same manner as the first embodiment, the medical device 1 of the modification 1 can reduce a risk of bacteria adhering to a single-use medical device after the medical device is taken out of the packaging material.
(Modification 2)

Next, a modification 2 of the first embodiment will be described.

Figure 7:
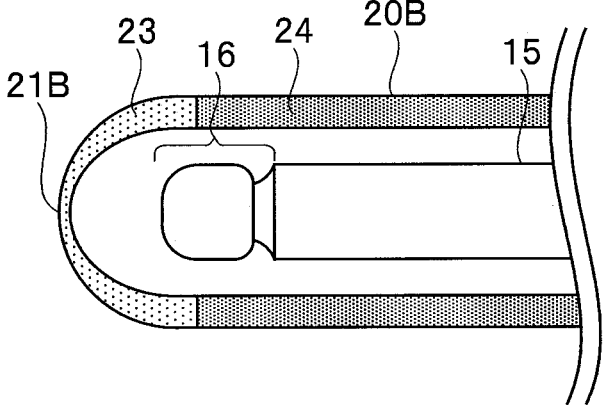
FIG. 7 is a diagram showing a configuration of a grasping portion of a treatment instrument according to a modification 2 of the first embodiment in a state in which the grasping portion is covered by a cover.

FIG. 7 is a diagram showing a configuration of a grasping portion of a treatment instrument according to the modification 2 of the first embodiment in a state in which the grasping portion is covered by a cover.

As shown in FIG. 7, a cover 20B includes a distal end portion 23 and a proximal end portion 24 provided on a proximal end side of the distal end portion 23. The cover 20B has a structure where the distal end portion 23 and the proximal end portion 24 are separate bodies, and the distal end portion 23 and the proximal end portion 24 are bonded and fixed by an adhesive agent or the like. At a distal end of the distal end portion 23, specifically, at a portion against which the grasping portion 16 abuts when the grasping portion 16 protrudes, an easy-to-open portion 21B having a smaller wall thickness than other portions is formed. In other words, the easy-to-open portion 21B is configured to have a lower strength than other portions of the cover 20B.

For a material of the distal end portion 23 of the cover 20B, a material is used that is torn more easily than a material of the proximal end portion 24. For example, the material of the distal end portion 23 is silicone rubber, and the material of the proximal end portion 24 is polyethylene. Note that the material of the distal end portion 23 is not limited to silicone rubber, and the material of the proximal end portion 24 is not limited to polyethylene. Provided that the material of the distal end portion 23 is a material that is torn more easily than the material of the proximal end portion 24, other materials may be used for the distal end portion 23 and the proximal end portion 24.

As described above, by using a material that is torn more easily than the material of the proximal end portion 24 for the material of the distal end portion 23 of the cover 20B, it is possible to easily push against and break the easy-to-open portion 21B by the grasping portion 16 when an operator causes the grasping portion 16 to protrude.

In the same manner as the modification 1, the cover 20B prevents the grasping portion 16 of the treatment instrument 10 from coming into contact with air in an operating room, body fluid of a patient or the like until the grasping portion 16 pushes against and breaks the easy-to-open portion 21B. As a result, it is possible to reduce a risk of bacteria adhering to the grasping portion 16 to an extremely low level. The first area 21B or 23 of the cover 20B has a first mechanical strength, and the second area 24 of the cover 20B has a second mechanical strength. The first mechanical strength is smaller than the second mechanical strength.

Therefore, in the same manner as the first embodiment, the medical device 1 of the modification 2 can reduce a risk of bacteria adhering to a single-use medical device after the medical device is taken out of the packaging material.

Second Embodiment

Next, a second embodiment will be described.

Figure 8:
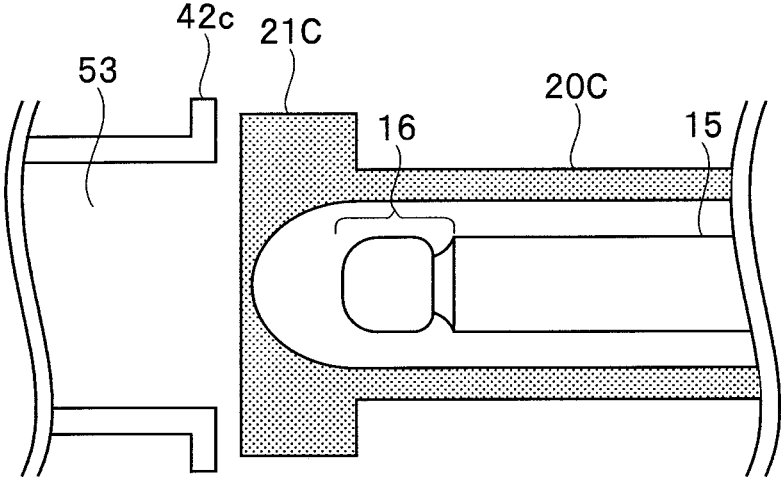
FIG. 8 is a diagram showing a configuration of a grasping portion of a treatment instrument according to a second embodiment in a state in which the grasping portion is covered by a cover.

FIG. 8 is a diagram showing a configuration of a grasping portion of a treatment instrument according to the second embodiment in a state in which the grasping portion is covered by a cover.

As shown in FIG. 8, a cover 20C includes an easy-to-open portion 21C at a distal end portion. An outer diameter of the easy-to-open portion 21C is larger than an outer diameter of a proximal end portion formed at a position closer to a proximal end side than the distal end portion. The outer diameter of the easy-to-open portion 21C is larger than an inner diameter of the treatment instrument insertion opening 42c, more specifically, an inner diameter of the treatment instrument channel 53 forming a first lumen. A distal end of the easy-to-open portion 21C, specifically, a portion against which the grasping portion 16 abuts when the grasping portion 16 protrudes, is configured to have a smaller wall thickness than other portions. In other words, the easy-to-open portion 21C is configured to have a lower strength than other portions of the cover 20C. The cover 20C may have a small diameter that is smaller than the easy-to-open portion 21C, the small diameter is provided at distally than the easy-to-open portion 21C to easily positioning the cover 20C relative to the treatment instrument insertion opening 42c. The distal end portion of the insertion portion 15 has an outer surface and an end surface. The cover 20C may completely surround the outer surface and the end surface. The cover 20C completely surrounds the outer surface and the end surface so as to encase the outer surface and the end surface within the cover 20C to maintain the encased portions sterilized. The cover 20C has a first portion 21C having a first outer diameter and a peripheral portion having a second outer diameter. The first portion 21C is distal to the peripheral portion. The treatment instrument 10 is configured to be inserted into a lumen 53 of the endoscope 40 via the treatment instrument insertion opening 42c. The first outer diameter of the first portion is larger than an inner diameter of the lumen 53 of the endoscope 40 or the treatment instrument insertion opening 42c.

When an operator further pushes on the insertion portion 15 of the treatment instrument 10 with the easy-to-open portion 21C of the cover 20C pushed against the treatment instrument insertion opening 42c, the grasping portion 16 pushes against and breaks the easy-to-open portion 21C. Therefore, the easy-to-open portion 21C is torn, thus forming an opening, so that the insertion portion 15 and the grasping portion 16 protrude from the cover 20C. The cover 20C including the easy-to-open portion 21C remains on an outer side of the treatment instrument insertion opening 42c, and the insertion portion 15 and the grasping portion 16 of the treatment instrument 10 are inserted into the treatment instrument channel 53.

With such a configuration, there is no possibility of the grasping portion 16 of the treatment instrument 10 coming into contact with air in an operating room, body fluid of a patient or the like until the grasping portion 16 of the treatment instrument 10 pushes against and breaks the easy-to-open portion 21C. As a result, it is possible to reduce a risk of bacteria adhering to the grasping portion 16 of the treatment instrument 10 to an extremely low level. The first area 21C of the cover 20C has a first cross-sectional area, and the second area of the cover 20C has a second cross-sectional area. The first cross-sectional area 21C is smaller than the second cross-sectional area. The first area 21C of the cover 20C has a first mechanical strength, and the second area of the cover 20C has a second mechanical strength. The first mechanical strength is smaller than the second mechanical strength.

Therefore, in the same manner as the first embodiment, the medical device 1 of the second embodiment can reduce a risk of bacteria adhering to a single-use medical device after the medical device is taken out of the packaging material.

Third Embodiment

Next, a third embodiment will be described.

Figure 9:
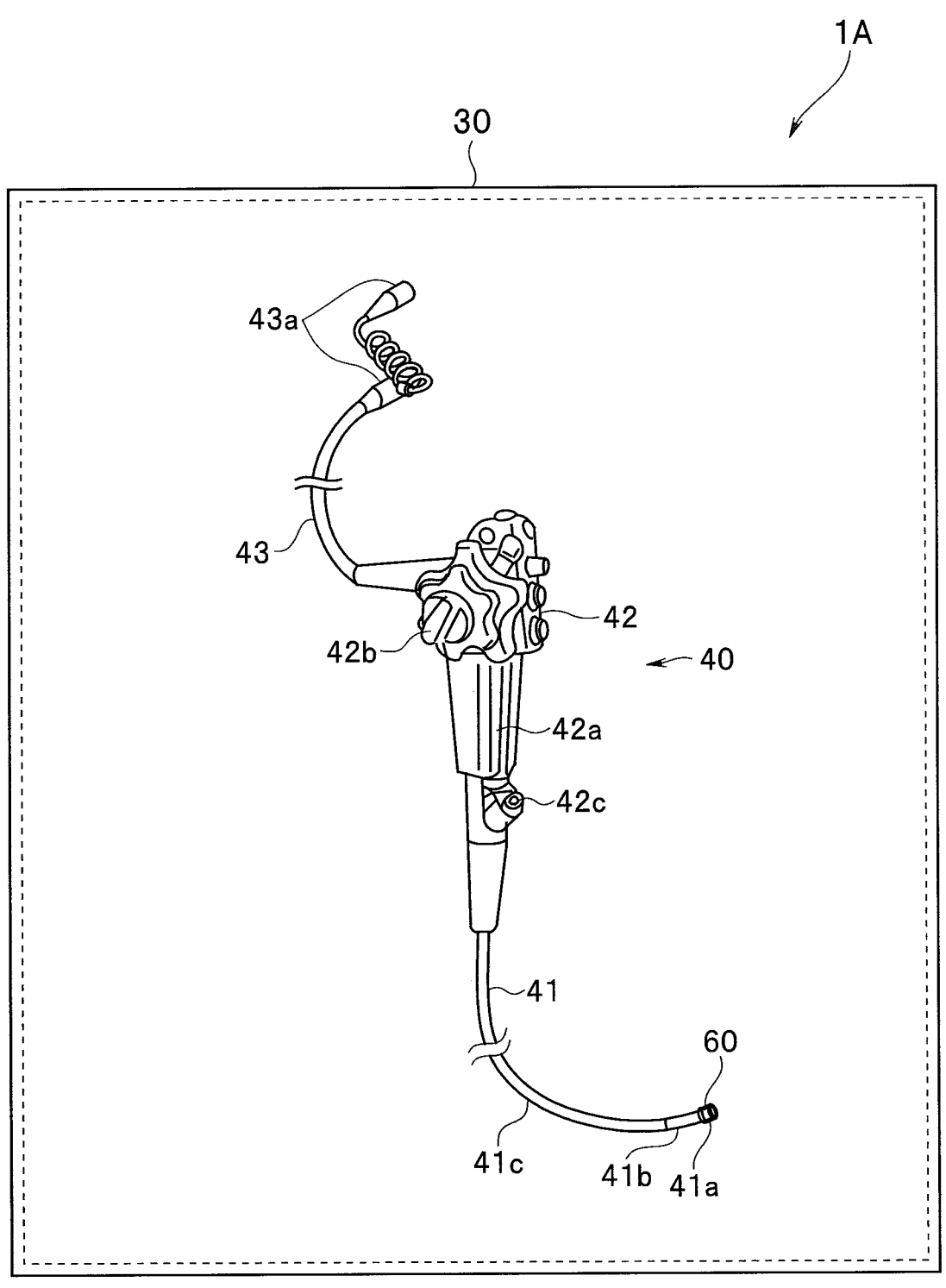
FIG. 9 is a diagram showing one example of an overall configuration of a medical device according to a third embodiment.
Figure 10:
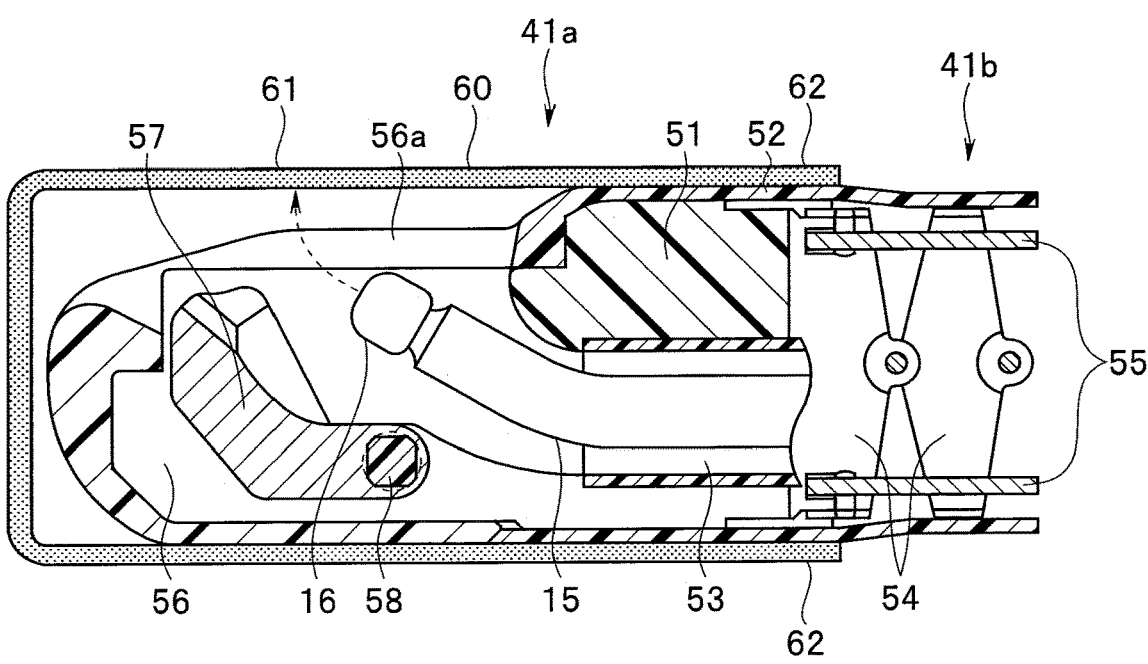
FIG. 10 is a diagram showing a configuration of a distal end forming portion of an endoscope according to the third embodiment in a state in which the distal end forming portion is covered by a cover.

FIG. 9 is a diagram showing one example of an overall configuration of a medical device according to the third embodiment, and FIG. 10 is a diagram showing a configuration of a distal end forming portion of an endoscope according to the third embodiment in a state in which the distal end forming portion is covered by a cover.

As shown in FIG. 9, a medical device 1A includes the endoscope 40 being a long insertion device to be inserted into the body. The distal end forming portion 41a of the endoscope 40 is covered by a cover 60. The endoscope 40 and the cover 60 to which sterilizing treatment is applied are disposed and sealed in the sterilization packaging material 30 to which sterilizing treatment is applied. The cover 60 is provided to cover the distal end forming portion 41a. However, for example, the cover 60 may be provided to cover, in addition to the distal end forming portion 41a, the active bending portion 41b, or the active bending portion 41b and the flexible tube portion 41c. The endoscope 40 includes the insertion portion 41 configured to be inserted into the subject. The cover 60 surrounding a distal end portion of the insertion portion 41, the cover 60 is configured to be teared by receiving external force so as to make an opening in the cover 60 for exposing the distal end portion. The distal end portion of the insertion portion 41 has an outer surface and an end surface. The cover 60 may completely surround the outer surface and the end surface. The cover 40 completely surrounds the outer surface and the end surface so as to encase the outer surface and the end surface within the cover 40 to maintain the encased portions sterilized. The insertion portion 41 includes the distal end portion and a proximal end portion, and the proximal end portion is not surrounded by the cover 60. The opening in the cover may be at a distal end of the cover 60.

The cover 60 is formed by a transparent member to allow an operator to perform an insertion operation while checking an endoscope image picked up by the endoscope 40. The cover 60 may be configured such that a transparent member is used only for a portion that falls within an angle of view of an image pickup device of an image pickup unit that picks up an image of an object.

As shown in FIG. 10, the cover 60 includes an easy-to-open portion 61 (first area) at the distal end portion. More specifically, the easy-to-open portion 61 is provided to face the opening 56a provided in one side surface of the distal end forming portion 41a. Easy-to-open processing is applied to the easy-to-open portion 61 to allow the easy-to-open portion 61 to be opened more easily than other portions. In other words, the easy-to-open portion 61 is configured to have a lower strength than other portions of the cover 60. The cover includes the first area 61, and a second area 62 adjacent the first area 61. The first area 61 is configured to be teared more easily than the second area 62, and the opening is formed in the first area 61. The opening may be formed at an interface of the first area 21 and the second area. The opening is formed in the first area 61 and extends around an entire circumference of the cover 60. The distal end of the insertion portion 41 is translatable, and the first area 61 of the cover 60 is located in a direction of protrusion of the insertion portion 41.

A proximal end portion of the cover 60 forms a watertight portion 62 bonded to a proximal end portion of the distal end forming portion 41a. Therefore, the cover 60 maintains watertightness of the distal end forming portion 41a of the endoscope 40.

An operator inserts the insertion portion 41 as far as a part to be treated in the body with the distal end forming portion 41a covered by the transparent cover 60. Thereafter, the operator inserts the treatment instrument 10 from the treatment instrument insertion opening 42c, and causes the treatment instrument 10 to protrude from the opening 56a via the treatment instrument channel 53, forming a second lumen, and to push against the easy-to-open portion 61, thus pushing against and breaking the easy-to-open portion 61. Therefore, an opening is formed in the easy-to-open portion 61 and the grasping portion 16 of the treatment instrument 10 protrudes from the formed opening, so that the operator can apply treatment to the part to be treated.

As described above, after the endoscope 40 is taken out of the sterilization packaging material 30, there is no possibility of the distal end forming portion 41a of the insertion portion 41 coming into contact with air in an operating room, body fluid of a patient or the like until the treatment instrument 10 pushes against and breaks the easy-to-open portion 61 of the cover 60. As a result, it is possible to reduce a risk of bacteria adhering to the distal end forming portion 41a of the insertion portion 41 to an extremely low level. The first area 61 of the cover 60 has a first cross-sectional area, and the second area 62 of the cover 60 has a second cross-sectional area. The first cross-sectional area is smaller than the second cross-sectional area. The first area 61 of the cover 60 has a first mechanical strength, and the second area 62 of the cover 60 has a second mechanical strength. The first mechanical strength is smaller than the second mechanical strength. The treatment instrument 10 is configured to move relative to the cover 60 in the longitudinal direction of the cover 60. A portion of the cover 60 that is teared to form the opening includes a distal end cover portion and a proximal end cover portion, and the proximal end cover portion is connected to the distal end cover with the opening.

Therefore, in the same manner as the first embodiment, the medical device 1A can reduce a risk of bacteria adhering to a single-use medical device after the medical device is taken out of the packaging material.

Fourth Embodiment

Next, a fourth embodiment will be described.

Figure 11:
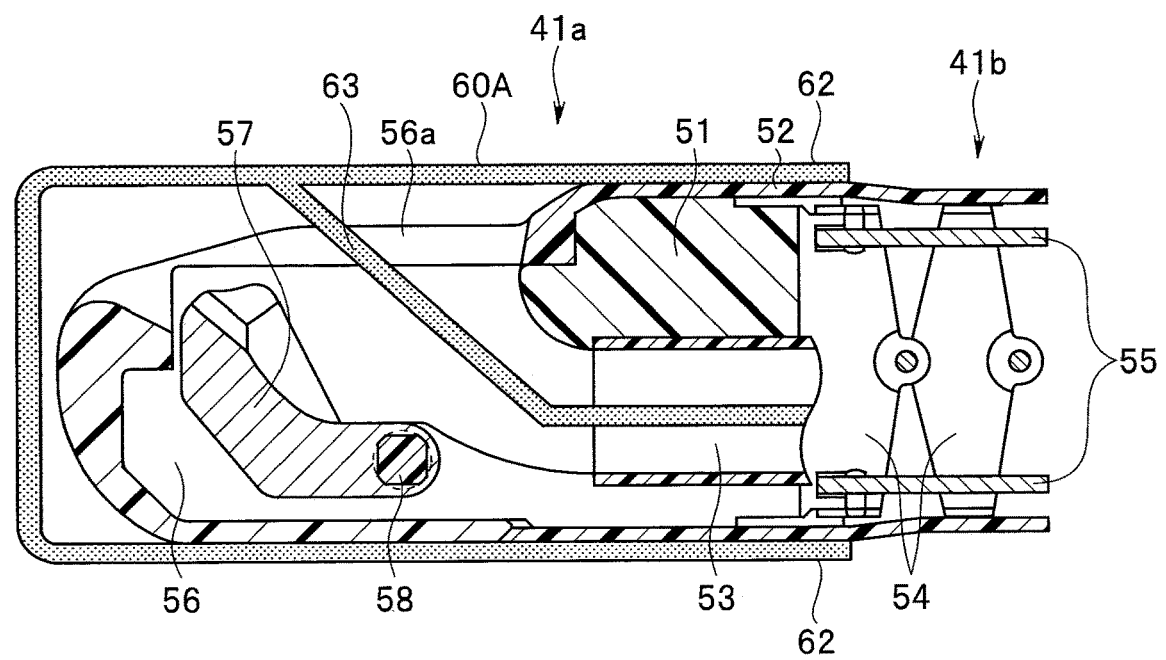
FIG. 11 is a diagram showing a configuration of a distal end forming portion of an endoscope according to a fourth embodiment in a state in which the distal end forming portion is covered by a cover.

FIG. 11 is a diagram showing a configuration of a distal end forming portion of an endoscope according to the fourth embodiment in a state in which the distal end forming portion is covered by a cover. In FIG. 11, components substantially equivalent to the corresponding components in FIG. 10 are given the same reference symbols, and the description of such components will be omitted.

As shown in FIG. 11, a cover 60A connected to a pulling string 63 (pulling member) forming a pulling member. The pulling member 63 may be part of the cover 60A. One end of the pulling string 63 is connected to an inner surface of the cover 60A. The pulling string 63 extends in the treatment instrument channel 53 from the inner surface of the cover 60A. The other end of the pulling string 63 is in a state of being pulled out from the treatment instrument insertion opening 42c via the treatment instrument channel 53. The cover 60A surrounding a distal end portion of the insertion portion 41, the cover 60A is configured to be teared by receiving external force so as to make an opening in the cover 60A for exposing the distal end portion. The distal end portion of the insertion portion 41 has an outer surface and an end surface. The cover 60A may completely surround the outer surface and the end surface. The cover 60A completely surrounds the outer surface and the end surface so as to encase the outer surface and the end surface within the cover 60A to maintain the encased portions sterilized. The insertion portion 41 includes the distal end portion and a proximal end portion, and the proximal end portion is not surrounded by the cover 60A. The opening in the cover 60A may be at a distal end 62 of the cover 60A. A portion of the cover 60A that is teared to form the opening includes a distal end cover portion and a proximal end cover portion. The proximal end cover portion is connected to the distal end cover with the opening.

An operator inserts the insertion portion 41 as far as a part to be treated in the body with the distal end forming portion 41a covered by the transparent cover 60A. Then, the operator pulls the other end of the pulling string 63, which is pulled out from the treatment instrument insertion opening 42c, toward a proximal end side of the insertion portion 41. With such operations, the watertight portion 62 peels off the distal end forming portion 41a, so that an opening is formed and the cover 60A is drawn into the treatment instrument channel 53 (lumen). By further pulling the other end of the pulling string 63, the operator takes the cover 60A out of the treatment instrument insertion opening 42c, thus removing the cover 60A from the endoscope 40. Thereafter, the operator inserts the treatment instrument 10 from the treatment instrument insertion opening 42c, and causes the grasping portion 16 to protrude from the opening 56a of the distal end forming portion 41a to apply treatment. The endoscope 40 includes the lumen 53 extending in the longitudinal direction of the endoscope 40 from a distal end portion of the insertion portion 41 to a proximal end of the endoscope 40. The pulling member 63 is inserted into the lumen 53 and extends from the distal end portion of the insertion portion 41 to the proximal end of the endoscope 40. The pulling member 63 is connected to the cover 60A. The pulling member 63 is configured to be pulled toward the proximal end of the endoscope 40 to create the external force to tear the cover 60A to make the opening. A portion of the cover 60A that is teared to make the opening is configured to be drawn through the lumen 53 and to be removed from the endoscope 40 by further pulling the pulling member 63 toward the proximal end of the endoscope 40.

As described above, after the endoscope 40 is taken out of the sterilization packaging material 30, there is no possibility of the distal end forming portion 41a of the insertion portion 41 coming into contact with air in an operating room, body fluid of a patient or the like until the pulling string 63 is pulled by the operator, so that the cover 60A peels off the distal end forming portion 41a. As a result, it is possible to reduce a risk of bacteria adhering to the distal end forming portion 41a of the insertion portion 41 to an extremely low level.

Therefore, in the same manner as the first embodiment, the medical device 1A can reduce a risk of bacteria adhering to a single-use medical device after the medical device is taken out of the packaging material.

The present disclosure is not limited to the above-mentioned embodiments, and various modifications and applications are conceivable without departing from the gist of the present disclosure.

Example 1. A medical device comprising:
an insertion device inserted into a body, the insertion device having a long shape;
a cover configured to cover at least a distal end portion of the insertion device; and
a sterilization packaging material sealed in a state in which the insertion device and the cover are disposed in the sterilization packaging material, wherein
the cover is opened by receiving a predetermined external force, and
the distal end portion is exposed from an opening.

Example 2. The medical device according to Example 1, wherein
the cover includes an easy-to-open portion that is opened more easily than another portion, and the opening is formed in the easy-to-open portion.

Example 3. The medical device according to Example 2, wherein
the opening is formed at a distal end of the cover.

Example 4. The medical device according to Example 3, wherein
the opening is a slit formed to extend in a radial direction of the cover.

Example 5. The medical device according to Example 1, wherein
the opening is a slit formed at a position closer to a proximal end side than a distal end of the cover, and formed to extend in a direction intersecting with a longitudinal direction of the cover.

Example 6. The medical device according to Example 4, wherein
the easy-to-open portion has an outer diameter larger than an outer diameter of a proximal end portion of the cover.

Example 7. The medical device according to Example 6, wherein
the insertion device is inserted into a first lumen formed in another insertion device, and
the easy-to-open portion has the outer diameter larger than an inner diameter of the first lumen.

Example 8. The medical device according to Example 2, wherein a second lumen is formed in the insertion device to extend in a longitudinal direction of the insertion device, the second lumen includes an opening portion at the distal end portion of the insertion device, and the opening portion is provided to face the easy-to-open portion.

Example 9. The medical device according to Example 1, wherein a lumen is formed in the insertion device to extend in a longitudinal direction of the insertion device, the cover includes a pulling member, and the pulling member is caused to extend in the lumen from an inner surface of the cover.

Example 10. The medical device according to Example 9, wherein when the pulling member is pulled toward a proximal side of the insertion device, the opening is formed in an easy-to-open portion of the cover.

Example 11. The medical device according to Example 10, wherein forming the opening allows the cover including the pulling member to be removed from the insertion device.

Example 12. The medical device according to Example 1, wherein the easy-to-open portion is configured to have a lower strength than another portion of the cover, and the opening is formed in the easy-to-open portion.

What is claimed is:

1. A medical device, comprising:

a first sterilized insertion device including an insertion portion configured to be inserted into a subject; and a cover surrounding a distal end portion of the insertion portion, the cover including a cover distal end portion separated in a radial direction from a distal end portion of the insertion portion, wherein the cover distal end portion includes a bottom portion and an opening portion, wherein the bottom portion is located to be contacted by the distal end portion of the insertion portion in an extended state of the insertion portion and to receive a force applied by the distal end portion of the insertion portion to the bottom portion, and wherein the opening portion is configured to be torn by the force applied by the distal end portion of the insertion portion to the bottom portion so as to make an opening in the cover for exposing the distal end portion.

2. The medical device according to claim 1, wherein the distal end portion of the insertion portion has an outer surface and an end surface, and wherein the cover completely surrounds the outer surface and the end surface.

3. The medical device according to claim 1, wherein the insertion portion includes the distal end portion and a proximal end portion, and wherein the proximal end portion is not surrounded by the cover.

4. The medical device according to claim 1, wherein the medical device further includes a sterilization packaging material, and wherein the first sterilized insertion device and the cover are sealed within the sterilization packaging material.

5. The medical device according to claim 1, wherein the cover includes:

a first area including the cover distal end portion, and a second area adjacent the first area, wherein the opening portion is configured to be torn more easily than the second area.

6. The medical device according to claim 5, wherein the first sterilized insertion device includes a lumen extending in a longitudinal direction of the first sterilized insertion device, wherein the lumen includes an opening at the distal end portion of the insertion portion, and wherein the bottom portion of the cover distal end portion faces the opening of the lumen.

7. The medical device according to claim 5, wherein the distal end of the insertion portion is translatable between a retracted state and the extended state, and wherein the first area of the cover includes a slit extending in a circumferential direction of the cover.

8. The medical device according to claim 5, wherein the first area of the cover includes a slit extending in a circumferential direction of the cover.

9. The medical device according to claim 5, wherein the first area of the cover has a first cross-sectional area, wherein the second area of the cover has a second cross-sectional area, and wherein the first cross-sectional area is smaller than the second cross-sectional area.

10. The medical device according to claim 5, wherein the opening portion of the cover distal end portion has a first mechanical strength, wherein the second area of the cover has a second mechanical strength, and wherein the first mechanical strength is smaller than the second mechanical strength.

11. The medical device according to claim 1, wherein the cover distal end portion has a first outer diameter and a peripheral portion of the cover has a second outer diameter, and wherein the first portion is distal to the peripheral portion.

12. The medical device according to claim 11, wherein the first insertion device is configured to be inserted into a lumen of a second insertion device, and wherein the first outer diameter of the cover distal end portion is larger than an inner diameter of the lumen of the second insertion device.

13. The medical device according to claim 5, wherein when the opening portion of the cover is torn to form the opening, the first area is connected to the second area.

14. The medical device according to claim 1, wherein the first sterilized insertion device is configured to move relative to the cover in a longitudinal direction of the cover.

15. The medical device according to claim 1, wherein the first sterilized insertion device is an endoscope.

16. The medical device according to claim 1, wherein the first sterilized insertion device is a treatment instrument.

* * * * *